United States Patent [19]

Howarth

[11] 4,006,358
[45] Feb. 1, 1977

[54] METHOD AND APPARATUS FOR MEASURING THE AMOUNT OF MOISTURE THAT IS ASSOCIATED WITH A WEB OF MOVING MATERIAL

[75] Inventor: John J. Howarth, Monte Sereno, Calif.

[73] Assignee: Measurex Corporation, Cupertino, Calif.

[22] Filed: June 12, 1975

[21] Appl. No.: 586,347

[52] U.S. Cl. .............................. 250/339; 250/341; 356/51
[51] Int. Cl.$^2$ .................... G01J 3/34; G01N 21/34
[58] Field of Search .......... 250/349, 350, 341, 339; 356/199, 51

[56] References Cited
UNITED STATES PATENTS

| 3,614,450 | 10/1971 | Hill et al. ........................... 250/350 |
| 3,790,796 | 2/1974 | Brunton et al. ..................... 250/349 |
| 3,803,414 | 8/1972 | Van Horne et al. ................. 250/341 |

Primary Examiner—Alfred E. Smith
Assistant Examiner—T. N. Grigsby
Attorney, Agent, or Firm—Flehr, Hohbach, Test, Albritton & Herbert

[57] ABSTRACT

An improved method and apparatus for measuring the moisture contained by a moving sheet of web material includes a water simulating filter in a typical dual wavelength moisture gauge which provides transmission ratios. The relationship between the change of ratios of various samples of the material with different moisture content with the change of the filter ratios when various layers of moist dirt are placed in the gauge transmission path is used to provide a corrected transmission ratio from which water weight can easily be determined. The method is also applicable to polymer coatings or similar substances.

11 Claims, 7 Drawing Figures

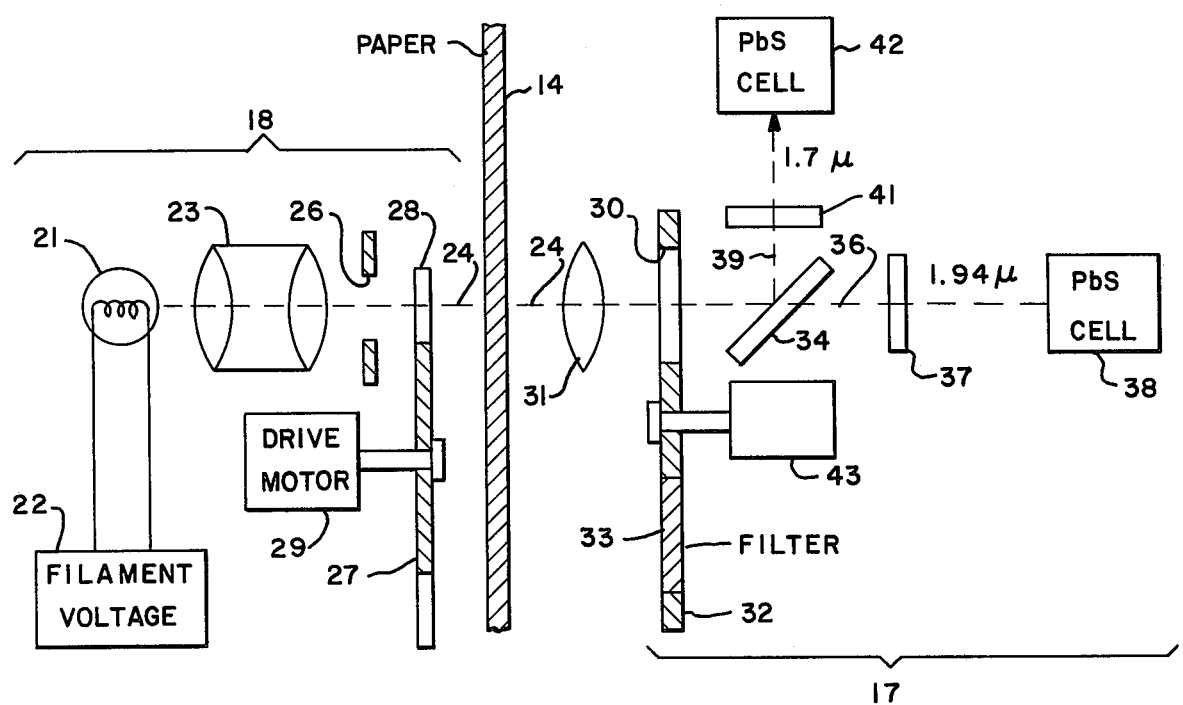
FIG.—1
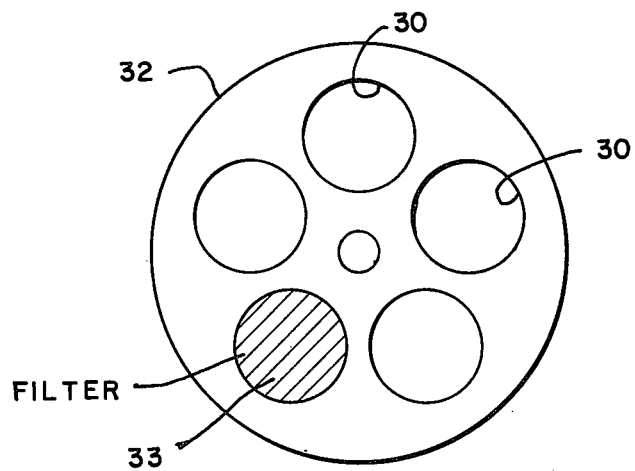
FIG.—1A

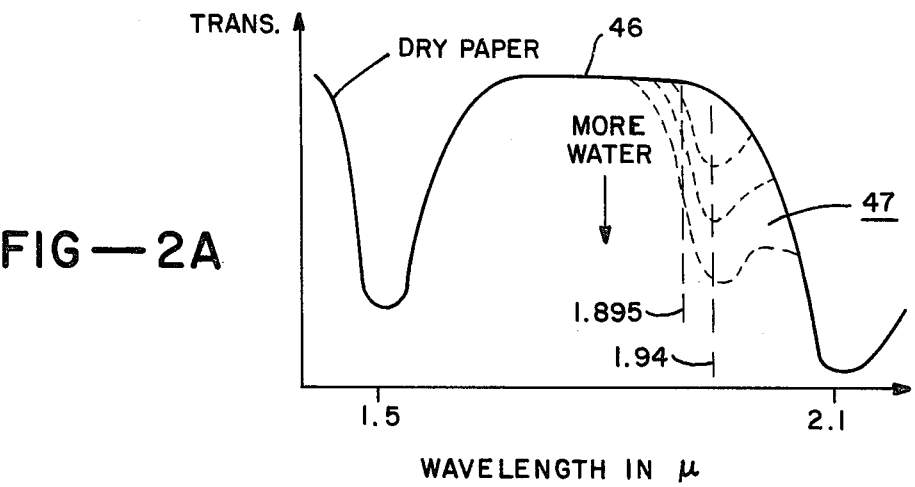
FIG.—2A
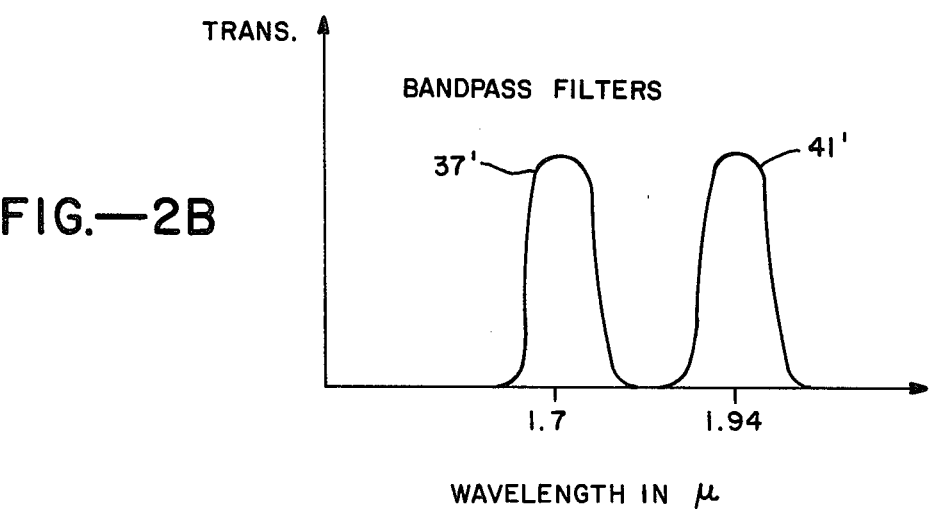
FIG.—2B
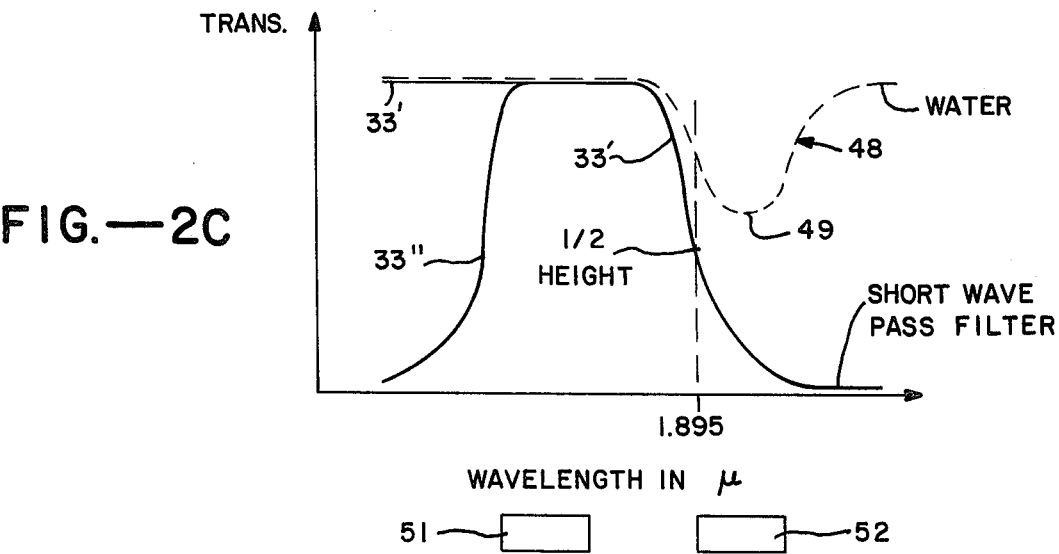
FIG.—2C

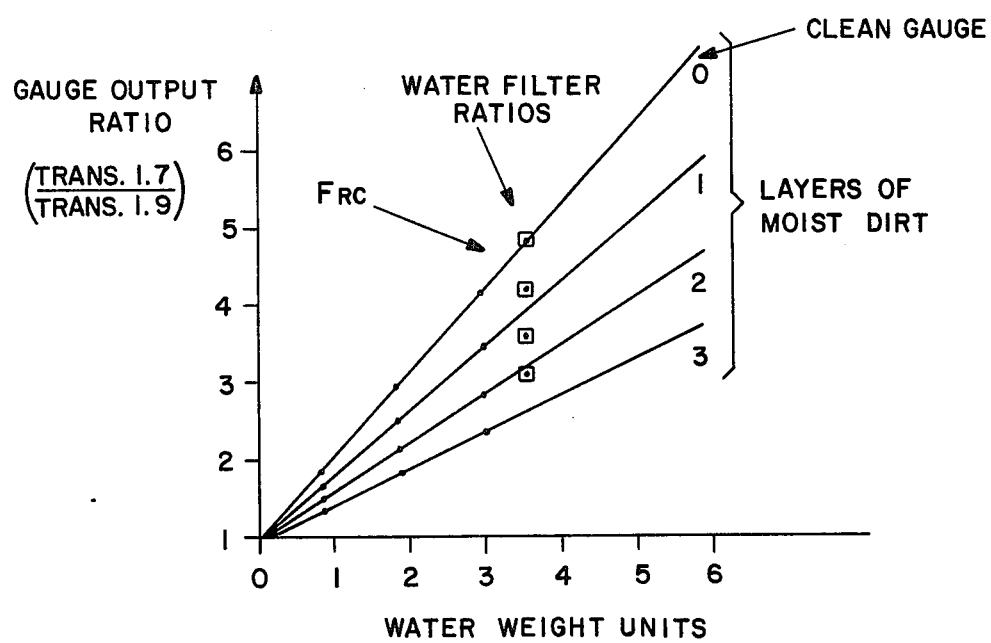
FIG.—3A
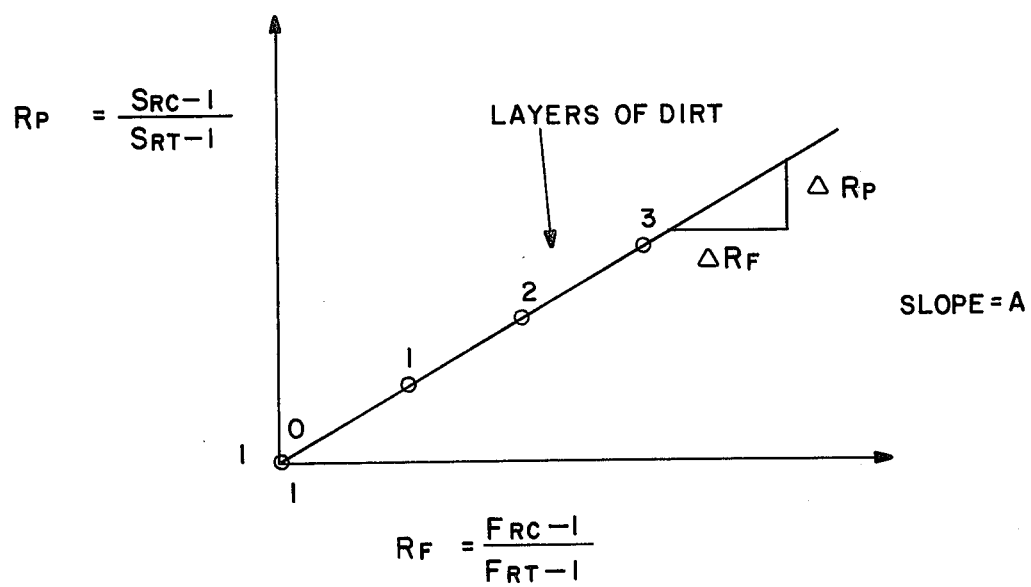
FIG.—3B

METHOD AND APPARATUS FOR MEASURING THE AMOUNT OF MOISTURE THAT IS ASSOCIATED WITH A WEB OF MOVING MATERIAL

BACKGROUND OF THE INVENTION

The present invention is directed to a method and apparatus for measuring the amount of moisture that is associated with a web of moving material. More particularly, the invention is directed toward measurement of water in paper as it is being manufactured by a paper making machine.

U.S. Pats. Nos. 3,641,349 and 3,675,019 both assigned to the assignee of the present application disclose moisture gauges for sheet material being manufactured by a paper making machine utilizing a dual wavelength technique. Normally such a gauge includes an infrared radiation source which emits radiation in two spectral bands. The first band of 1.7 microns impinges upon the paper and the amount of transmission through the paper or reflected from the paper is a function of certain parameters of it. It is known that in the case of a spectral band encompassing 1.7 microns or 1.8 microns that this wavelength region is relatively insensitive to the moisture content of the paper. However, in the spectral band including 1.94 microns lies within the absorption band of the water or moisture contained by the paper, it is relatively sensitive. Thus, the ratio of the two spectral bands is a function of the amount of water in the paper.

As illustrated by the foregoing U.S. Pat. Nos. 3,641,349 and 3,675,019, normally several factors contribute to inaccuracies in measurement. These include electronic drift and effects due to dirty environment from which the moisture gauge operates. Such factors necessitated various standardization and/or calibration schemes. However, even with the foregoing, error was still present in measurement of moisture content.

OBJECT AND SUMMARY OF THE INVENTION

It is, therefore, a general object of the present invention to provide an improved method and apparatus for measuring the amount of substance that is associated with a web of moving material.

In accordance with the above object there is provided a method utilizing the foregoing dual wavelength measurement technique and also apparatus in which a filter which simulates a predetermined amount of substance and has a spectrally similar characteristic is utilized. Such filter is selectively interposed between the radiation source and detectors during a standardization interval.

BRIEF DESCRIPTION OF THE DRAWINGS

FIG. 1 is a schematic representation partially in block diagram form and partially in cross section of a portion of the apparatus embodying the present invention;

FIG. 1A is a plan view of one of the elements of FIG. 1;

FIGS. 2A through 2C are characteristic curves relating a wavelength to attenuation useful in understanding the present invention; and FIGS. 3A and 3B are curves used in the method of the present invention.

DETAILED DESCRIPTION OF THE PREFERRED EMBODIMENT

The optical system of FIG. 1 is similar to that shown in the above-mentioned U.S. Pat. No. 3,641,349 except for the use of the water simulating filter which will be discussed in detail below. In general, the components included in an upper gauging head which scans across the moving web of material in the paper making machine are shown by the bracket 17 and the lower gauging head by the bracket 18. Lower head 18 contains a tungsten light source 21 having a filament voltage source 22 providing radiation both in the spectral band including 1.7 microns and in the spectral band including 1.94 microns. Radiation from the radiation source is collimated by an optical system schematically shown at 23 the beam path being indicated by the dashed line 24 extending through an aperture and then through a chopper wheel 27.

The beam path 24 extends through the moving paper sheet or web 14 which in a manner well-known in the art and approximately according to Beer's law, attenuates the infra-red radiation emission from source 21. As discussed above, the radiation in the wavelength of 1.94 microns is much more sensitive to moisture in the paper than the 1.7 microns of radiation. After the radiation is transmitted through paper sheet 14 it is detected by upper detector unit 17 which includes a collimating lens 31 in the beam path 24. It, of course, should be understood that the infrared radiation need not be transmitted from one side of the paper to the other and that both the source and radiation detector may be on the same side of the moving sheet of paper and a reflection technique utilized. Moreover, for more accurate measurement, for many types of paper, diffusing windows may be used as disclosed and claimed in U.S. Pat. No. 3,793,524 in the name of the present inventor.

Referring still to the detector unit 17, the attenuated radiation on beam path 24 passes through a filter assembly 32 which in normal operation has an open window 30 to allow free passage of the beam to the beam splitter 34. At that point one portion 36 of the split beam passes through a bandpass filter 37 which has a bandpass centered around 1.94 microns and the beam is then detected by a lead sulfide cell 38. The other portion of the split beam 39 passes through a bandpass filter 41 centered around a wavelength of 1.7 microns and thereafter to a second lead sulfide detection cell 42.

Filter assembly 32 as shown in plan view in FIG. 1A, in addition to the open windows 30, includes a filter 33 which as will be discussed in detail below simulates the spectral characteristics of water. It is rotated by the solenoid 43. Alternatively, the filter wheel may be replaced by a rotary solenoid which selectively moves filter 33 in and out of the beam path.

In accordance with the invention the desired spectral characteristic of filter 33 is described more particularly in conjunction with FIGS. 2A through 2C. As illustrated in FIG. 2A, the solid curve 46 indicates the absorption of dry paper in the infrared wavelength region and the dashed family of curves at 47 indicates a change in this characteristic as more water is added to the dry paper. As is well-known in the art, the lowest point, i.e., strongest water absorption, of these curves occurs at substantially 1.94 microns. The half heights (i.e., 50% transmission) of the water curves occur substantially along a vertical line located at 1.895 microns. Therefore, the filter 33 is chosen, as indicated by filter characteristic 33' in FIG. 2C to have a half transmission which is 1.895 ± 0.01 microns. Other specifications which are somewhat less exact is a 90% transmission at 1.85 microns and a 10% transmission at 1.95 microns; i.e., the filter slope must be approximately correct.

FIG. 2C illustrates a filter characteristic 33' of the short wave pass type, which is believed to be ideal, where in the 1.7 micron range the characteristic is flat. Alternatively, as indicated by the curve 33'' a bandpass filter could be utilized since here, as illustrated in FIG. 2B, due to the 1.7 micron bandpass filter 37 (See FIG. 1 and FIG. 2B) shorter wavelengths are not relevant. The bandpass characteristic 37' of the 1.7 micron filter 37 is not critical. However, the bandpass 41' for 1.94 micron filter 41 is critical since the effective cutoff at the low frequency longer wavelength end of the filter should match the cutoff of the short wave pass filter characteristic 33'. Thus, the opposite slope or half of the water curve indicated at 48 in FIG. 2C is irrelevant since the 1.94 bandpass extends only substantially to the minimum bottommost portion 49 of the water curve. Thus, only one-half of the water curve need effectively be matched.

With respect to the 1.7 transmission point of the filter 33 variations of ±10% can be easily tolerated. In addition fairly good transmission should occur at this point typically in the range of 80 to 90%. Thus, in FIG. 2C the strips 51 and 52 show the two filter bands which should be matched.

The use of the filter 33 in the standardization method incorporating the present invention is best understood with reference to FIGS. 3A and 3B. In order to construct the curves of 3A a plurality of samples of sheet material of different known amounts of moisture are provided. As is well known in the paper making art such samples are produced by use of clear plastic waterproof bags so that the samples will maintain a constant moisture content over a reasonable period of time. After the foregoing samples are placed between the radiation source and detectors a transmission ratio of the 1.7 spectral band compared to the 1.9 spectral band is measured for each sample and produces the curve labeled "clean gauge." The ratio is the vertical axis and water weight is the horizontal axis. Next at substantially the same time the water simulating filter 33 is inserted in the beam path by itself and a ratio reading taken, labeled $F_R$. It is assumed that this ratio lies on the clean gauge curve. Since the curve is linear starting at the origin only a single moisture sample need be used in practice.

The clean gauge curve of FIG. 3A is also standardized by a standardization ratio $R_S$ with no samples or filter present by a typical off sheet measurement well-known in the art.

A layer of moist tissue which simulates one layer of moist dirt is taped across an aperture in the lower head, (see the U.S. Pat. No. 3,793,524), adjacent to the position of sheet 14, and allowed to stabilize its moisture content. Standardized ratios of the various samples and the filter 33 are then measured to produce the curve 1 for one layer of moist dirt. The values of course are also standardized by the standardization ratio $R_S$. These values are plotted as illustrated in FIG. 3A.

The above steps are then repeated for two layers of moist dirt and then three layers producing the curves indicated. Each layer of moist dirt is, in general terms, a convenient carrier (tissue) containing a stable amount of substance (moisture) which is to be measured. The water filter ratio points as well as the ratios of the various samples all lie on vertical lines since their water weight by definition has not changed. However, it should be noted that the curves of the plot of FIG. 3A illustrates how normal standardization is not totally effective in a moisture gauge system. The basic problem of standardization which is solved in the present invention is separation of gauge errors due to variations in the lamp source, detectors or the electronics from errors due to the buildup of a film of water on the measuring unit itself. The layers of moist dirt, of course, represent this buildup.

Inspection of FIG. 3A illustrates that the gauge output ratios (1.7/1.9) start at the one level and increase linearly while the water weights start at zero. It is obvious that unit or progressive increases in water weight absorb a progressively decreasing amount of the remaining energy of the radiation; i.e., there is a non-equal absorption of energy by equal units of water. Thus, when the optical signals are reduced by moist dirt, the typical standardization normalizes the signal to correct the zero point but will not correct the foregoing non-equal absorption. This is accomplished by use of a new calibration line of FIG. 3B.

In accordance with the invention the information of FIG. 3A, which is obtained at the factory calibration, is utilized to construct the curve of FIG. 3B. In other words, the change of filter ratios, $R_F$, due to the placement of the successive layers of moist dirt are related to the similar change of sample ratios. Specifically in FIG. 3B the vertical axis $R_P$ is the ratio of the slope of the clean gauge to the slope of the dirty gauge with the various layers of moist dirt. Similarly, the filter ratio $R_F$ is a clean versus dirty ratio. The curves 1, 2, 3 are therefore normalized with the clean gauge curve. Thus the origin of FIG. 3B in effect is the clean gauge curve and is a ratio of one for both vertical and horizontal axes. Thereafter for various layers of dirt indicated as 0, 1, 2, and 3, the curve of FIG. 3B can be constructed. In fact, it is a straight or linear curve which greatly simplifies its use in the determination of the final corrected filter ratios. Depending on the gauge system however it may not necessarily be linear.

In any case with the linear curve of FIG. 3B, which has a constant slope A, such information can provide a corrected transmission ratio to provide for an accurate moisture measurement. From a mathematical standpoint this is done as follows. The slope of A is calculated as shown in equation (1).

$$A = \frac{\Delta R_P}{\Delta R_F} = \frac{R_P - 1}{R_F - 1} = \frac{\left(\frac{S_{RC}-1}{S_{RT}-1}\right)-1}{\left(\frac{F_{RC}-1}{F_{RT}-1}\right)-1} \quad (1)$$

where,
$S_{RC}$ = sample ratio clean
$S_{RT}$ = sample ratio measured
$A$ = slope of Δ sample/Δ filter ratio
$F_{RC}$ = filter ratio in clean gauge-time zero
$F_{RT}$ = filter ratio at last standardize That is, any pair of $R_P$ and $R_F$ values can have a 1 subtracted from them and provide the slope since the origin is 1,1. The corrected sample ratio is $$S_{RC} = 1 + (S_{RT} - 1)\left[1 + A\left\{\left(\frac{F_{RC}-1}{F_{RT}-1}\right) - 1\right\}\right] \quad (2)$$

With the corrected sample ratio $S_{RC}$ the clean gauge curve of FIG. 3A yields the exact water weight.

Therefore to summarize, the moisture gauge of the present invention is first calibrated at the factory in that the slope A of the curve of FIG. 3B is provided along with the initial filter ratio $F_{RC}$. When the gauge is installed on site the standardized transmission ratio, $S_{RT}$, of the sheet material actually being measured is determined along with the present filter ratio, $F_{RT}$, and by use of the simple relationship of equation (2) $S_{RC}$ is determined. Finally from the clean gauge curve of FIG. 3A, which can be expressed in a stored table in a computer, the actual water weight is determined.

With the method of the present invention a sample of tissue having a basis weight of approximately 12/3000 with varying amounts of water was measured with the results as shown below.

| | | OLD | | NEW | |
|---|---|---|---|---|---|
| % Water | Ratio Gauge Clean | Ratio Gauge Dirty | % Error of Reading | Water Filter Corrected Ratio | % Error of Reading |
| 2 | 1.14313 | 1.12765 | 10.81 | 1.1412 | 1.35 |
| 4 | 1.19229 | 1.18494 | 7.20 | 1.20457 | 2.65 |
| 6 | 1.28107 | 1.25308 | 9.96 | 1.27993 | 4.06 |
| 8 | 1.36166 | 1.32332 | 10.60 | 1.35763 | 1.11 |
| 10 | 1.42862 | 1.38159 | 10.97 | 1.42209 | 1.52 |

The column labeled "NEW" shows almost an order of magnitude improvement when compared to the prior art technique designated "OLD." All readings have been standardized.

The technique of the present invention is also useful for determining the weight of coatings applied to paper; for example, polythene. Such coatings normally have a characteristic as shown in FIG. 2A similar to water. Thus, similar errors occur due to the presence of dirt containing some of the coating material in analogy to moist dirt.

Since the coating material is more stable than water the filter may simulate the substance or material by using an actual piece of the material; e.g. polythene.

What is claimed is:

1. A method for measuring the amount of substance that is associated with a web of moving material where a radiation source emits a first spectral band of radiation that impinges on the material and is strongly sensitive to the substance in the material and a second spectral band of radiation which is less sensitive to said substance, and where first and second detection means are respectively responsive to the intensities of radiation of the first and second spectral bands which are reflected from or transmitted through the material, the method comprising the following steps:
   a. providing at least one sample of said material with a known amount of said substance;
   b. placing said sample between said radiation source and detectors and measuring the ratio of the radiation received by the first and second detector means;
   c. providing a filter which simulates a predetermined amount of substance the filter being spectrally similar to the frequency sensitivity of said substance to said radiation over a predetermined frequency band;
   d. placing said filter between said radiation source and detectors and measuring said ratio;
   e. determining the relationship between a change of sample ratios and a change of filter ratios due to placement of a successive plurality of nominal layers of a carrier containing some of said substance between said source and detectors; and
   f. utilizing the relationship of step (e) to provide a corrected ratio for an unknown sheet material.

2. A method as in claim 1 where said substance is moisture.

3. A method for measuring the amount of moisture that is associated with a web of moving material where a radiation source emits a first spectral band of radiation that impinges on the material and is strongly sensitive to the moisture in the material and a second spectral band of radiation which is less sensitive to said moisture, and where first and second detection means are respectively responsive to the intensities of radiation of the first and second spectral bands which are reflected from or transmitted through the material, the method comprising the following steps:
   a. providing at least one sample of said material with a known amount of moisture;
   b. placing said sample between said radiation source and detectors and measuring the ratio of the radiation received by the first and second detector means;
   c. providing a filter which simulates a predetermined amount of moisture the filter being spectrally similar to the frequency sensitivity of moisture to said radiation over a predetermined frequency band;
   d. placing said filter between said radiation source and detectors and measuring said ratio;
   e. measuring a standardization ratio, $R_S$, with no sample or filter present;
   f. plotting the standardized ratios of said samples and filter, $F_{RC}$, versus moisture amount;
   g. placing a nominal one layer of a carrier containing moisture between said radiation source and detectors and measuring a standardization ratio, $R_S$;
   h. placing said sample and filter between said radiation source and detector and measuring said ratios;
   i. plotting said ratios in step (h) after standardization;
   j. repeating steps (g), (h) and (i) but with a nominal two layers of carrier containing moisture;
   k. utilizing said plots of step (j) to construct a curve relating said filter ratio for a given number of said nominal layers of carrier to the slope of the plot of said samples for the same number of layers;
   l. storing both the slope, A, of the curve of step (k) and said filter ratio, $F_{RC}$, with no layers of carrier;
   m. measuring the standardized ratio $S_{RT}$ of an unknown sheet material, and the present filter ratio $F_{RT}$ and utilizing said slope to obtain a corrected ratio directly relatable to moisture amount in said unknown material by use of plot of step (f).

4. A method as in claim 3 where $F_{RT}$ is taken in an off sheet mode where said web is not present said measurement being accomplished every several scans of said radiation source.

5. Apparatus for measuring the amount of moisture that is associated with a web of moving material including a radiation source which emits a first spectral band of radiation that impinges on the material and is strongly sensitive to the moisture in the material and a second spectral band of radiation which is much less sensitive to said moisture, and including first and second detector means which are respectively responsive to the intensities of radiation of the first and second spectral bands which are reflected from or transmitted through the material, said apparatus comprising a filter which is spectrally similar to the frequency sensitivity of moisture to said radiation over a predetermined frequency band and means for selectively interposing said filter between said radiation source and said detectors.

6. Apparatus as in claim 5 together with a bandpass filter between said first detector means and said source for filtering said first spectral band of radiation having a sharp cutoff at a wavelength which coincides with the minimum of the frequency sensitivity of said moisture.

7. Apparatus as in claim 5 where said filter has a constant characteristic in said second spectral band.

8. Apparatus as in claim 5 where said filter is of the short wave pass type having a frequency sensitivity matching only one-half of the frequency band of said moisture frequency sensitivity together with a bandpass filter between said first detector means and said source for cutting off the other half of said moisture frequency band.

9. Apparatus as in claim 5 where said filter is of the short wave pass type.

10. Apparatus as in claim 9 where the half-height of said filter is closely matched to an equivalent portion of said frequency sensitivity of said moisture.

11. Apparatus as in claim 10 where said half-height of said filter is substantially 1.895 microns.

* * * * *